(12) United States Patent
Ahmadi et al.

(10) Patent No.: US 11,964,090 B2
(45) Date of Patent: Apr. 23, 2024

(54) SYSTEMS AND METHODS OF GAS REMOVAL FROM A WEARABLE DEVICE

(71) Applicant: QIDNI LABS INC., Buffalo, NY (US)

(72) Inventors: Morteza Ahmadi, Buffalo, NY (US); Clarence Graansma, Buffalo, NY (US)

(73) Assignee: QIDNI Labs, Inc., Buffalo, NY (US)

( * ) Notice: Subject to any disclaimer, the term of this patent is extended or adjusted under 35 U.S.C. 154(b) by 436 days.

(21) Appl. No.: 17/434,536

(22) PCT Filed: Feb. 28, 2020

(86) PCT No.: PCT/US2020/020475
§ 371 (c)(1),
(2) Date: Aug. 27, 2021

(87) PCT Pub. No.: WO2020/176879
PCT Pub. Date: Sep. 3, 2020

(65) Prior Publication Data
US 2022/0126010 A1    Apr. 28, 2022

Related U.S. Application Data

(60) Provisional application No. 62/812,198, filed on Feb. 28, 2019.

(51) Int. Cl.
*A61M 1/36*      (2006.01)
*B01D 19/00*     (2006.01)

(52) U.S. Cl.
CPC ........ *A61M 1/3627* (2013.01); *A61M 1/3626* (2013.01); *B01D 19/0031* (2013.01);
(Continued)

(58) Field of Classification Search
CPC .............. A61M 1/3627; A61M 1/3626; A61M 2205/18; A61M 2205/3327;
(Continued)

(56) References Cited

U.S. PATENT DOCUMENTS

| 4,690,762 A | * | 9/1987 | Katsura | .............. B01D 19/0031 |
| | | | | 210/512.1 |
| 2003/0056646 A1 | * | 3/2003 | Tanaka | ............... B01D 53/0454 |
| | | | | 96/111 |

(Continued)

OTHER PUBLICATIONS

Search Report and Written Opinion for Application No. PCT/US2020/020475, dated May 20, 2020, 19 pages.

*Primary Examiner* — Robert A Hopkins
*Assistant Examiner* — Qianping He (57) ABSTRACT

Systems, devices, and method for gas removal from a wearable device are provided. The systems comprise a gas removal filter having an inlet, a fluid outlet, and a vent port. The gas removal filter comprises a filter mesh between the inlet and outlet, the filter mesh configured to allow only liquid phase material through the filter mesh. The systems also comprises a gas detector for detecting gas in the gas removal filter; a orientation sensor for determining an orientation of the gas removal filter; a transducer protector filter having a first side and a second side, the transducer protector filter on fluid communication with the vent port of the gas removal filter; a pressure transducer in fluid communication with the second side of the transducer protector filter; and an gas removal pump in fluid communication with the second side of the transducer protector filter.

13 Claims, 5 Drawing Sheets

(52) U.S. Cl.
CPC ..... *B01D 19/0063* (2013.01); *A61M 2205/18* (2013.01); *A61M 2205/3327* (2013.01); *A61M 2205/3344* (2013.01); *A61M 2205/7527* (2013.01); *A61M 2209/088* (2013.01)

(58) Field of Classification Search
CPC .. A61M 2205/3344; A61M 2205/7527; A61M 2209/088; B01D 19/0031; B01D 19/0063
USPC .............................................................. 95/8
See application file for complete search history.

(56) References Cited

U.S. PATENT DOCUMENTS

| | | |
|---|---|---|
| 2004/0009097 A1 | 1/2004 | Stringer et al. |
| 2005/0247203 A1* | 11/2005 | Chevallet ............ A61M 1/3627 96/209 |
| 2010/0094193 A1 | 4/2010 | Gura et al. |
| 2011/0126714 A1 | 6/2011 | Bruger et al. |
| 2012/0116283 A1 | 5/2012 | Nilsson |
| 2017/0136170 A1 | 5/2017 | Weiting et al. |
| 2017/0232173 A1 | 8/2017 | Perry et al. |
| 2019/0099536 A1 | 4/2019 | Zhao |

* cited by examiner

SYSTEMS AND METHODS OF GAS REMOVAL FROM A WEARABLE DEVICE

CROSS REFERENCE TO RELATED APPLICATION AND CLAIM OF PRIORITY

This application is a national phase application under 35 U.S.C. § 371 of International Application No. PCT/US2020/020475 filed Feb. 28, 2020, which claims priority to U.S. provisional patent application No. 62/812,198 filed on Feb. 28, 2019, the entire contents of each are hereby incorporated by reference in their entirety.

FIELD

The disclosure related generally to fluid processing systems and methods including wearable ambulatory, and more particularly to systems and methods for detecting air in a fluid return line and automatically purging the air therefrom.

BACKGROUND

One of the safety devices required in all existing dialysis systems is a method of preventing air bubbles generated in the dialysis process from being returned into the patient's circulation. Existing systems use a drip chamber wherein the blood exits from the bottom of the chamber and the air rises to the top. In these systems, the equipment operator visually checks the blood level in the chamber and raises the level manually or with a manually controlled air pump from time to time. These systems use a level detector to verify that the drip chamber level is always above the safe level. These systems must always be maintained in a vertical orientation in order to function safely.

Arterial filters have been used instead of bubble traps to remove gas from blood in cardiopulmonary bypass (CPB) and extracorporeal membrane oxygenation (ECMO)systems. These filters must be in an vertical orientation in order to remove the accumulated air in the chamber, however, they will continue to prevent air from passing through the arterial filter even when they are not in the vertical orientation.

Wearable systems by their portable nature may not always be in the vertical orientation.

SUMMARY

Wearable renal therapy devices offer patients with end-stage renal disease a method of treatment that reduces the productive time lost that is devoted to dialysing in dialysis clinics. Wearable devices also offer existing home dialysis patients more freedom to travel outside of their homes.

In an aspect, the systems and methods of the present disclosure may permit a gas removal filter to be used safely in a medical device such as a wearable renal therapy device with minimal user intervention. The systems of method of the present disclosure may also ensure that gas is removed from gas removal filter only when the filter is in the upright orientation.

In one aspect, the disclosure describes a system for gas removal from a wearable device. The system comprises a gas removal filter having a inlet, a fluid outlet, and a vent port, the gas removal filter comprising: a filter mesh between the fluid inlet and fluid outlet, the filter mesh configured to allow liquid phase material through the filter mesh and restrict gas phase material passing through the filter mesh; a gas detector for detecting gas in the gas removal filter; a orientation sensor for determining an orientation of the gas removal filter; a transducer protector filter having a first side and a second side, the transducer protector filter on fluid communication with the vent port of the gas removal filter; a pressure transducer in fluid communication with the second side of the transducer protector filter; and an gas removal pump in fluid communication with the second side of the transducer protector filter. In an embodiment, the orientation sensor comprises an accelerometer In any one of the above embodiments, the system comprises a controller comprising a non-transitory computer readable storage medium having program code embodied therewith, the program code readable/executable by a computer, processor or logic circuit to perform a method comprising: detecting gas in the gas removal filter based on a signal from the gas detector; detecting orientation of the gas removal filter based on a signal from the orientation sensor; measuring a pressure in the gas removal filter based on a signal from the pressure transducer.

In any one of the above embodiments, the system comprises detecting gas in the gas removal filter with an ultrasonic gas detector configured to detect gas in the vent tubing. In an embodiment, the detecting orientation of the gas removal filter comprises detecting the orientation of the gas removal filter relative to the ground.

In any one of the above embodiments, the system comprises removing gas from the gas removal filter when: gas is detected in the gas removal filter, and the orientation of the vent tube is at an angle enabling gas within the gas removal filter to flow to the vent port. In an embodiment, the angle is generally perpendicular to the ground.

In any one of the above embodiments, the system comprises terminating the removal of gas from the gas removal filter when a pressure drop is measured at the pressure transducer.

In any one of the above embodiments, the system comprises sending a signal to an alarm to when a pressure increase is measured above venous pressure.

In any one of the above embodiments, the system comprises removing gas from the gas removal filter with the gas removal pump.

In any one of the above embodiments, the system comprises measuring the duration and flowrate of gas removed by the gas removal pump, and calculating the volume or mass of gas removed.

In any one of the above embodiments, the system comprises a mount coupled to the gas removal chamber, the mount providing at least two vectors of rotation which permit the gas removal filter to tilt and roll respectively, the mount comprising at least one motor for rotating the gas removal filter about the at least two vectors of rotation. In an embodiment, the system comprises measuring at least one of a tilt and a roll of the gas removal filter; calculating an output for the at least one motor to move the gas removal chamber to an upright orientation; and driving the at least one motor to rotate the gas removal filter to an upright orientation.

Embodiments may include combinations of the above features.

In another aspect, the disclosure describes a system for gas removal from a wearable device. The system comprises a gas removal filter having a inlet, a fluid outlet, and a vent port, the gas removal filter, the gas removal filter configured to separate gas and liquid based on their relative density; a gas detector for detecting gas in the gas removal filter; a orientation sensor for determining an orientation of the gas removal filter; a transducer protector filter having a first side and a second side, the transducer protector filter on fluid communication with the vent port of the gas removal filter;

a pressure transducer in fluid communication with the second side of the transducer protector filter; an gas removal pump in fluid communication with the second side of the transducer protector filter; a mount coupled to the gas removal chamber, the mount providing at least two vectors of rotation which permit the gas removal filter to tilt and roll respectively, the mount comprising at least one motor for rotating the gas removal filter about the at least two vectors of rotation; and a controller comprising a non-transitory computer readable storage medium having program code embodied therewith, the program code readable/executable by a computer, processor or logic circuit to perform a method. The method comprises: detecting gas in the gas removal filter based on a signal from the gas detector; detecting orientation of the gas removal filter based on a signal from the orientation sensor; measuring a pressure in the gas removal filter based on a signal from the pressure transducer; measuring at least one of a tilt and a roll of the gas removal filter; calculating an output for the at least one motor to move the gas removal chamber to an upright orientation; and driving the at least one motor to rotate the gas removal filter to an upright orientation; removing gas from the gas removal filter when: gas is detected in the gas removal filter, and the orientation of the vent tube is at an angle enabling gas within the gas removal filter to flow to the vent port.

In an embodiment, the system comprises a filter mesh positioned between the fluid inlet and fluid outer.

In another embodiment, the filter mesh is a clot removal filter.

Embodiments may include combinations of the above features.

In another aspect, the disclosure describes a device for gas removal from a wearable device, the device comprising: a gas removal filter having a inlet, a fluid outlet, and a vent port, the gas removal filter comprising: a filter mesh between the fluid inlet and fluid outlet, the filter mesh configured to allow liquid phase material through the filter mesh and restrict gas phase material passing through the filter mesh; a gas detector for detecting gas in the gas removal filter; a orientation sensor for determining an orientation of the gas removal filter; a transducer protector filter having a first side and a second side, the transducer protector filter on fluid communication with the vent port of the gas removal filter; a pressure transducer in fluid communication with the second side of the transducer protector filter; and an gas removal pump in fluid communication with the second side of the transducer protector filter.

In another aspect, the disclosure describes a method of removing gas from a wearable device, the method comprising: detecting gas in a gas removal filter; detecting an orientation of the gas removal filter; measuring a pressure in the gas removal filter; and removing gas from the gas removal filter when: gas is detected in the gas removal filter, and the orientation of the vent tube is at an angle enabling gas within the gas removal filter to flow to the vent port.

In an embodiment, the method comprises terminating the removal of gas from the gas removal filter when a pressure drop is measured in vent tubing of the gas removal filter.

In another embodiment, the method comprises sending a signal to an alarm to when the pressure increases above venous pressure or when a time interval between valid upright orientation detections exceeds a set value.

In another embodiment, the method comprises measuring a time interval beginning when removing gas from the gas removal filter is initiated and ending when gas is no longer detected in the gas removal filter; and calculating the volume or mass of gas removed from the gas removal filter from the time interval and flow rate of the gas removed.

In another embodiment, the method comprises detecting an absence of gas in the gas removal filter; injecting gas back into the gas removal filter for a length of time; and sending a signal to an alarm when an absence of gas is detected after the length of time.

In another embodiment, the method comprises receiving a measured orientation signal of the gas removal filter; calculating an output for a motor to move the gas removal chamber to an upright orientation; sending a signal to the motor comprising the output; and driving the motor to move the gas removal chamber to an upright orientation.

In another aspect, the disclosure provides a computer program product for controlling gas removal from a wearable device system, the computer program product comprising a non-transitory computer readable storage medium having program code embodied therewith, the program code readable/executable by a computer, processor or logic circuit to perform the method as described above.

Embodiments may include combinations of the above features.

Further details of these and other aspects of the subject matter of this application will be apparent from the detailed description included below and the drawings.

DESCRIPTION OF THE DRAWINGS

In the figures, embodiments are illustrated by way of example. It is to be expressly understood that the description and figures are only for the purpose of illustration and as an aid to understanding.

Reference is now made to the accompanying figures, in which:

FIG. 2b illustrates a cross-sectional view along the line A-A in FIG. 2a;

DETAILED DESCRIPTION

Although terms such as "maximize", "minimize" and "optimize" may be used in the present disclosure, it should be understood that such term may be used to refer to improvements, tuning and refinements which may not be strictly limited to maximal, minimal or optimal.

The term "connected" or "coupled to" may include both direct coupling (in which two elements that are coupled to each other contact each other) and indirect coupling (in which at least one additional element is located between the two elements).

The term "substantially" as used herein may be applied to modify any quantitative representation which could permissibly vary without resulting in a change in the basic function to which it is related.

The term "ground" used as used herein may applied to a plane perpendicular to the force of gravity at the location of the systems and methods described herein.

The term "upright orientation" or "upright position" as used herein refer to the orientation, position, or angle of the gas removal filter in which gas within the gas removal filter will rise toward a vent port to escape the gas removal filter(s) described herein. In an example, the upright orientation indicates that the vent port of the gas removal filter disclosed herein is positioned substantially in a direction opposing to the ground and substantially perpendicular with respect to the ground.

In the embodiments described herein, air is an example gas. Both air and gas may be used interchangeable in the description of the systems and methods described herein.

Aspects of various embodiments are described through reference to the drawings.

Figure 1:
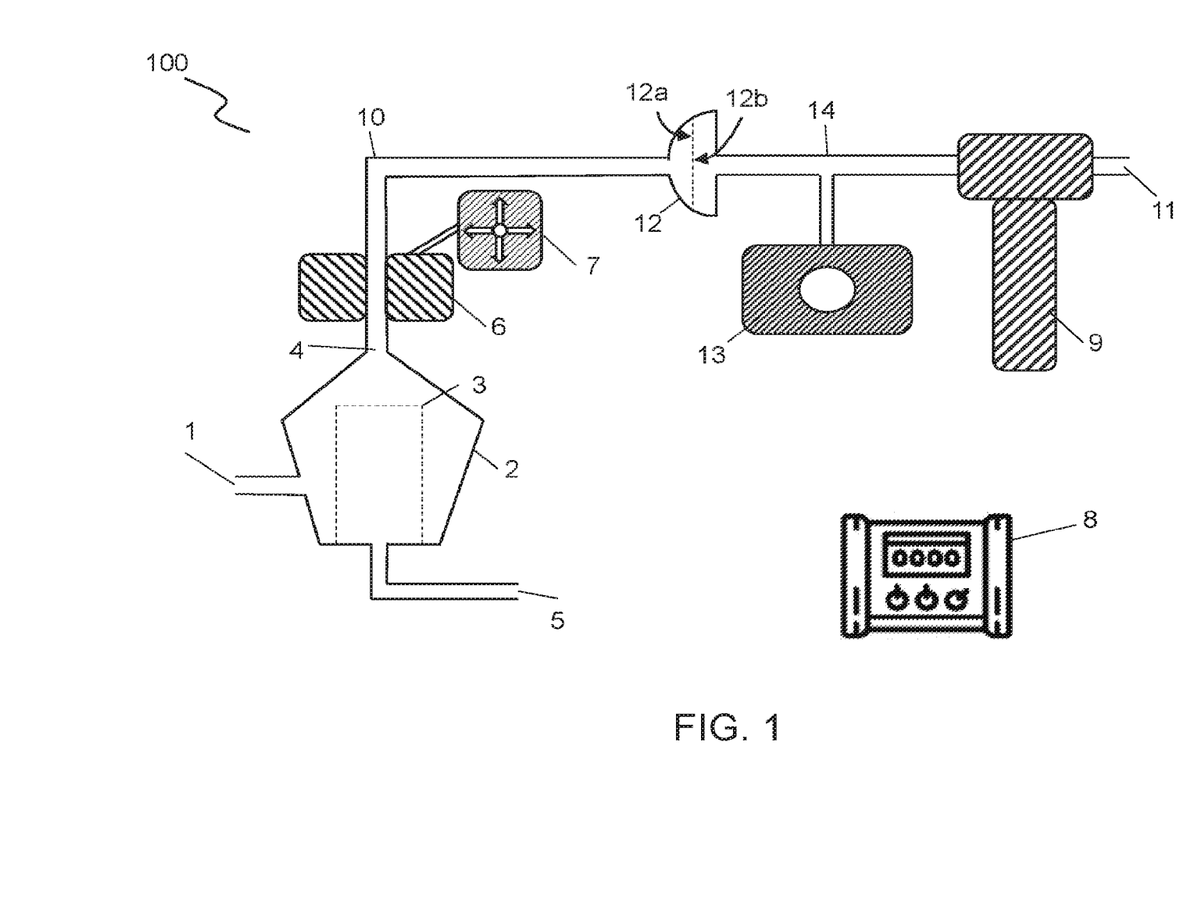
FIG. 1 illustrates a system for gas removal from a wearable device, in accordance with an embodiment of the present application.

FIG. 1. illustrates an example gas removal system 100 according to the present disclosure. As shown, a system 100 for gas removal from a wearable device (not shown) is illustrated. The system 100 is configured to be part of the wearable device such that the system is portable as a constituent part of the wearable device. System 100 comprises an gas removal filter 2 having a inlet 1, a fluid outlet 5, and a vent port 4. The gas removal filter 2 comprises a filter mesh 3 between the inlet 1 and fluid outlet 5. Filter mesh 3 may be configured to allow liquid phase material through the filter mesh 3 and restrict gas phase material passing through filter mesh 3. In an embodiment, filter mesh 3 has a pore size of 40-micron mesh which is configured to prevent the passage of air through the mesh but allow the passage of blood while minimizing pressure drop. In another embodiment, pore size of filter mesh 3 is selected such that surface tension of gas bubbles entering inlet 1 maintains the integrity of the gas bubbles in gas removal filter 2 to prevent the gas bubbles from breaking apart and passing through filter mesh 3. As gas bubbles accumulate in gas removal filter 2, the gas bubbles may agglomerate together into larger bubbles and tend to rise in the upward direction (opposite to ground). Filter mesh 3 may be any form of suitable material and not limited to polyester. Filter mesh may be pleated to increase the available surface area of filter mesh. The pleats may also contribute to increase rigidity of the filter mesh. Further, a pleated mesh may promote a pattern of flow of process fluid across the filter mesh 3 to remove accumulated bubbles from a surface of filter mesh 3 to improve the tendency of the bubbles of the surface of filter mesh 3 to rise within gas removal filter 2.

In an example, inlet 1 may receive fluid, e.g. blood, containing gaseous bubbles of air which cannot pass through filter mesh 3. As such, filter mesh 3 defines a volume within gas removal filter 3 in which only liquid phase material is permitted, the volume in fluid communication with fluid outlet 5. In an embodiment, the gas removal filter 2 may be a Cardiomed™ ultrafil 40 provided by Cardiomed Supplies Inc., or a Baby Sherlock arterial filter bubble trap provided by Eurosets™. In an example, gas removal filter 2 may be configured to received a maximum flow rate in a range of 300 mL/min to 1.5 L/min of process fluid. In another example, gas removal filter 2 may be configured to received a maximum flow rate of 300 mL/min. In another example, gas removal filter 2 may have at least one of the following characteristics: a priming volume of 40 mL; a polycarbonate housing material; and a filter mesh surface area of about 120 square cm.

Gas removal system 100 may also comprise a gas detector 6 configured to detect gas, e.g. air, in the gas removal system 100. As illustrated in FIG. 1, gas detector 6 may be positioned on vent tubing 10 which is in fluid communication with vent port 4 of gas removal filter 2. In a non-limiting example, gas detector may be an air bubble detector 071-06403 4MM provided by TE Connectivity Measurement Specialties Inc. and supplied by Digikey™ Part #223-1899-ND.

Accelerometer 7 may be provided for determining an orientation of the gas removal filter 2. Detection of the orientation of the gas removal filer may permit detection of when certain methods described herein may be performed, such as when vent port 4 is positioned to allow gas entrained in fluid from inlet 1 to move toward vent port 4 due to its lower relative density in comparison to the fluid. In an example, accelerometer 7 may be configured to detect the orientation of the gas removal filter relative to the ground. Continuing the example, accelerometer 7 may be configured to detect when vent port 4 is positioned in an upright orientation, i.e. in a direction opposing to the ground and generally perpendicular with respect to the ground. Accelerometer 7 itself may be positioned adjacent to gas removal filter 2. A non-limiting example of an accelerometer is ICM-20602 provided by TDK InvenSense™ supplied by Digikey™ Part #1428-1060-1-ND. In some embodiments, accelerometer 7 may be replaced by another type of orientation sensor. Such an orientation sensor may include, for example, a suitable combination of one or more accelerometers, a gyroscope, and a magnetometer.

Vent port 4 of gas removal filter 2 may be in fluid communication with a transducer protector filter 12. The transducer protector filter 12 may have a first side 12a and a second side 12b, where the transducer protector filter 12 is in fluid communication with the vent port of the gas removal filter. As shown in FIG. 1, vent tubing 10 fluidly connects transducer protection filter 2 with vent port 4 of gas removal filter 2. A pressure transducer 13 and a gas removal pump 9 may be in fluid communication with the second side 12b. Pressure transducer 13 and air removal pump 9 may be connected to transducer protector filter 12 via T-fitting 14. An non-limiting example pressure transducer may be Merit Sensor™ MSS100 provided by Merit Sensor Systems, Inc. An non-limiting example of a gas removal pump is Welco™ WPM1 Stepper motor peristaltic pump provided by Welco Co., Ltd. Other gas pumps (such as DC motor peristaltic pumps) may also be used if they can be calibrated for accuracy of air volume removal by the addition of an encoder wheel for instance.

Figure 2A:
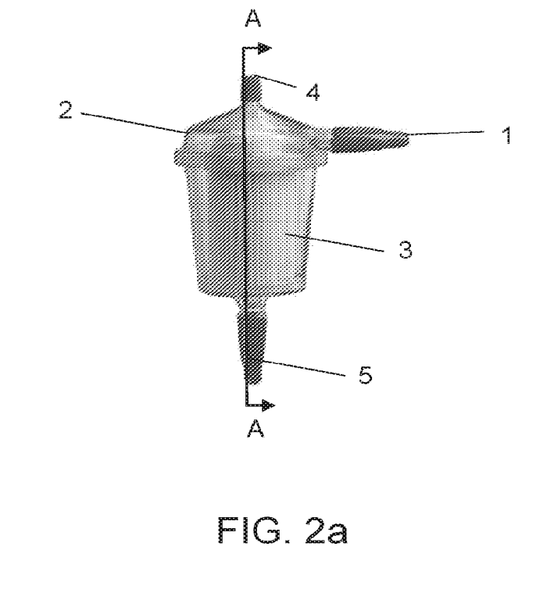
FIG. 2a illustrates a perspective view of a gas removal filter.
Figure 2B:
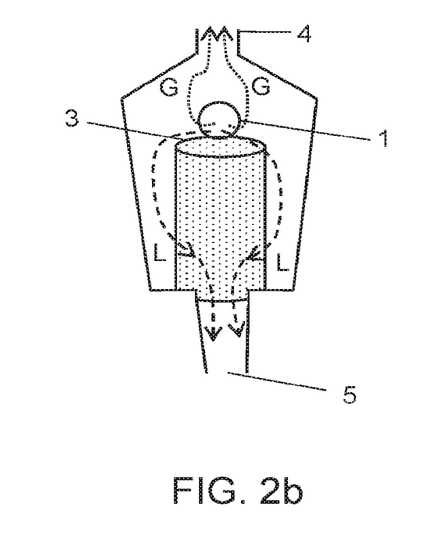

When in use, process fluid enters the gas removal system 100 via gas removal filter fluid inlet 1 into the gas removal filter 2. The process fluid could be blood, plasma, dialysate, or some other fluid. An example gas removal filter 2 is illustrated in FIG. 2a an 2b. The process fluid then passes through the gas removal filter mesh 3 for removing the gas (e.g. air) bubbles. As shown in FIG. 2b, the flow path of the gas G generally may rise upon entering gas removal filter 2 and/or after coming in contact with filter mesh 3. The flow path of liquid L entering gas removal filter 2 may accumulate in the gas removal filter and gradually pass through filter mesh 3. In an example, as gas bubbles accumulate to the top the gas removal filter 2, when the gas removal filter 2 is in the upright orientation, a fluid level within the gas removal filter drops as gas/air accumulates at vent port 4 which is positioned at or near the top of the gas removal filter 2. The process fluid exits the air removal filter 2 via an outlet port 5 of gas removal filter 2.

Gas detector 6, e.g. an ultrasonic air detector, may be positioned on vent tube 10 proximate to gas removal filter 2. Accelerometer 7 detects the orientation of the gas removal filter 2 and/or vent tube 10. When the orientation of the gas removal filter 2 and vent port 4/vent tube 10 is substantially upright or vertical with respect to ground, and there is also air detected at gas detector 6, controller 8 may be configured to direct gas removal pump 9 to remove gas from vent tubing 10 out to gas exit port 11 until gas is no longer detected by gas detector 6. Transducer protector filter 12 may protect the process fluid from bacterial contamination from external air and also may protect the gas removal pump 9 and pressure transducer 13 from fouling. In an embodiment, transducer protector filer 12 may comprise a hydrophobic filter material.

Figure 4:
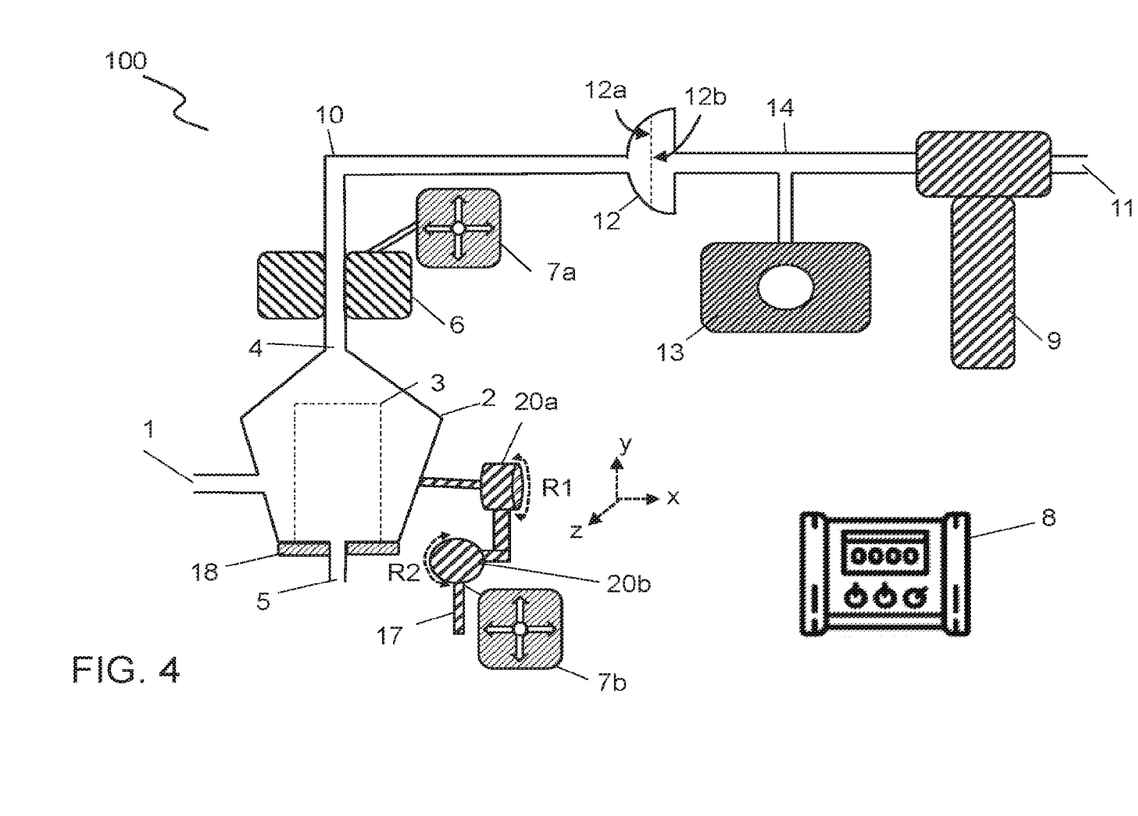
FIG. 4 illustrates an another example system for gas removal from a wearable device, in accordance with an embodiment of the present application, the system comprising gimbal and a gas removal filter.
Figure 5:
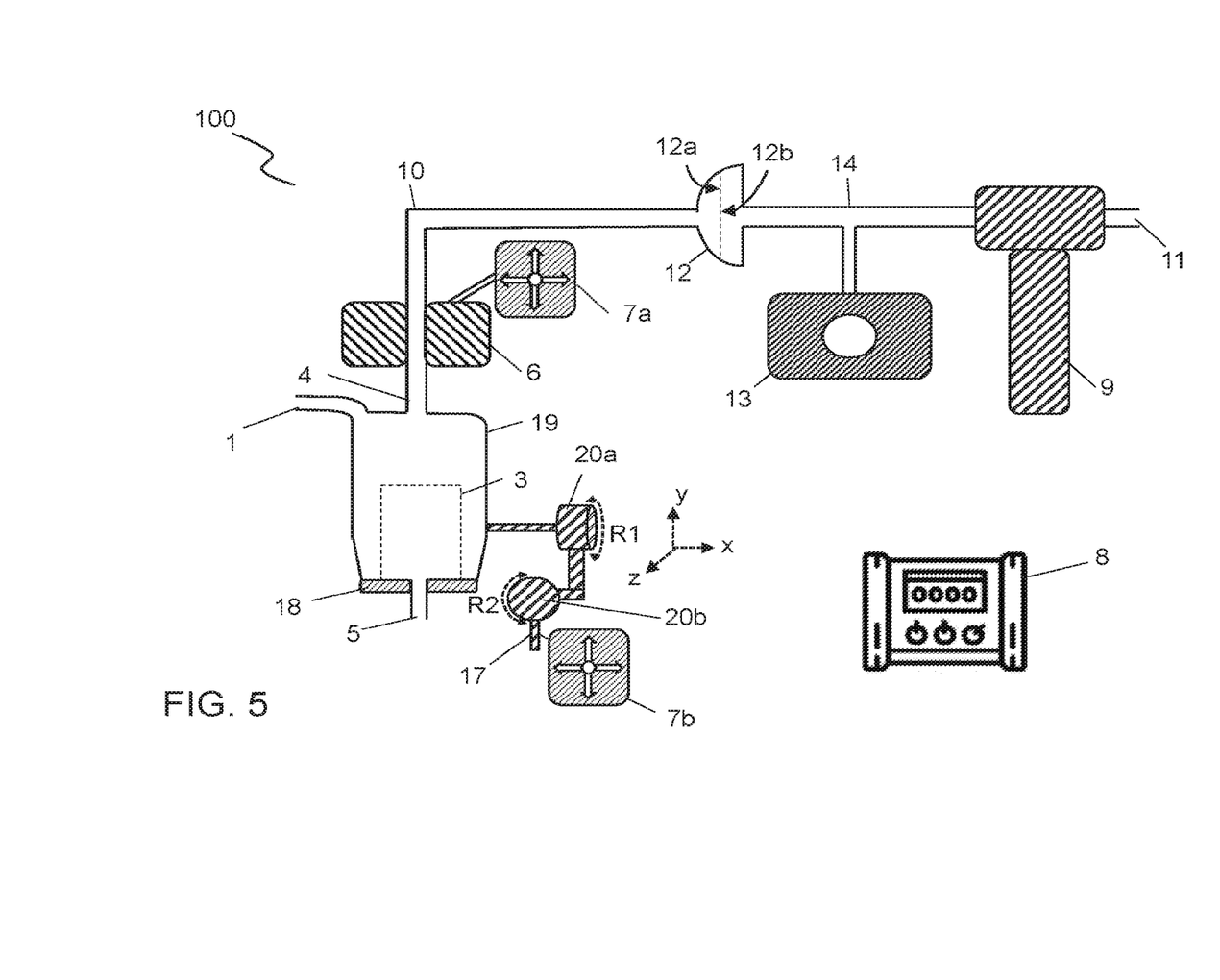
FIG. 5 illustrates an another example system for gas removal from a wearable device, in accordance with an embodiment of the present application, the system comprising a gimbal and a gas removal filter configured as a drip chamber.

FIG. 4 illustrates another embodiment of system 100. As shown, an example gas removal system 100 also comprises a mount 17 providing two vectors of rotation, R1 and R2, which allow gas removal filter 2 to tilt and roll respectively. In an embodiment, mount 17 would restrict gas removal filter 2 from panning to mitigate against twisting or otherwise flexing the components of system 100 which may cause damage. In the example illustrated in FIG. 4, mount 17 is configured to rotate about vector R1, i.e. tilt about the x-axis, and rotate about vector R2, i.e. roll about the z-axis. In an embodiment, mount 17 is a gimbal. Mount 17 may be configured to automatically correct the orientation of gas removal filter 2. Mount 17 may comprise a motors 20*a*, 20*b*, e.g. motorized servo controls, to rotate gas removal filter 2 about tilt and roll vectors R1 and R2 to maintain a substantially upright orientation of gas removal filter 2. The tubing of inlet 1, vent tubing 10, and outlet 5 may be made of flexible and resilient material to accommodate the rotation of gas removal filter 2 relative to mount 17. Mount 17 may be reversibly coupled to gas removal filter 2 using clamps or any other known connecting means. In an embodiment, system 100 may comprise at least two accelerometers 7*a*, 7*b* (or other type of orientation sensors) where accelerometers 7*a* and 7*b* are configured to measure the tilt and roll of gas removal filter 2 respectively (or vice-versa). As shown in FIG. 4, accelerometer 7*a* may be positioned on gas removal filter 2, and accelerometer 7*b* may be positioned on mount 17. In an embodiment, system 100 may comprise a counterweight 18 configured to keep gas removal filter 2 in an upright orientation. As shown in FIGS. 4 and 5, counterweight 18 may be positioned on a bottom surface of gas removal filter 2.

FIG. 5 illustrates another example gas removal system 100 comprising the elements of the example system illustrated in FIG. 4; however, gas removal filter 2 is a drip chamber 19. Drip chamber 19 may function in a similar manner as a dialysis drip chamber such that a liquid level accumulates within drip chamber 19 with a gas (air) layer above the liquid and the gas and liquid are separated based on their relative density. Inlet 1 may be positioned at or near the top of drip chamber 19 such that process liquid entering drip chamber 19 will drip into drip chamber 19 and accumulate therein. Gas, e.g. air, within the process liquid may rise within drip chamber 19 into the gas (air) layer. Filter mesh 3 may be provided within drip chamber 19. In an embodiment, filter mesh 3 is a clot removal filter configured to prevent blood clots from passing out of outlet 5.

By integrating a gas removal system 100 into a wearable device, i.e. a portable dialysis device, embodiments of the present disclosure may be configured for a user to wear the wearable device for extended periods of time and receive treatment from the wearable device which may require removal of gas (e.g. air) from the wearable device.

Figure 3:
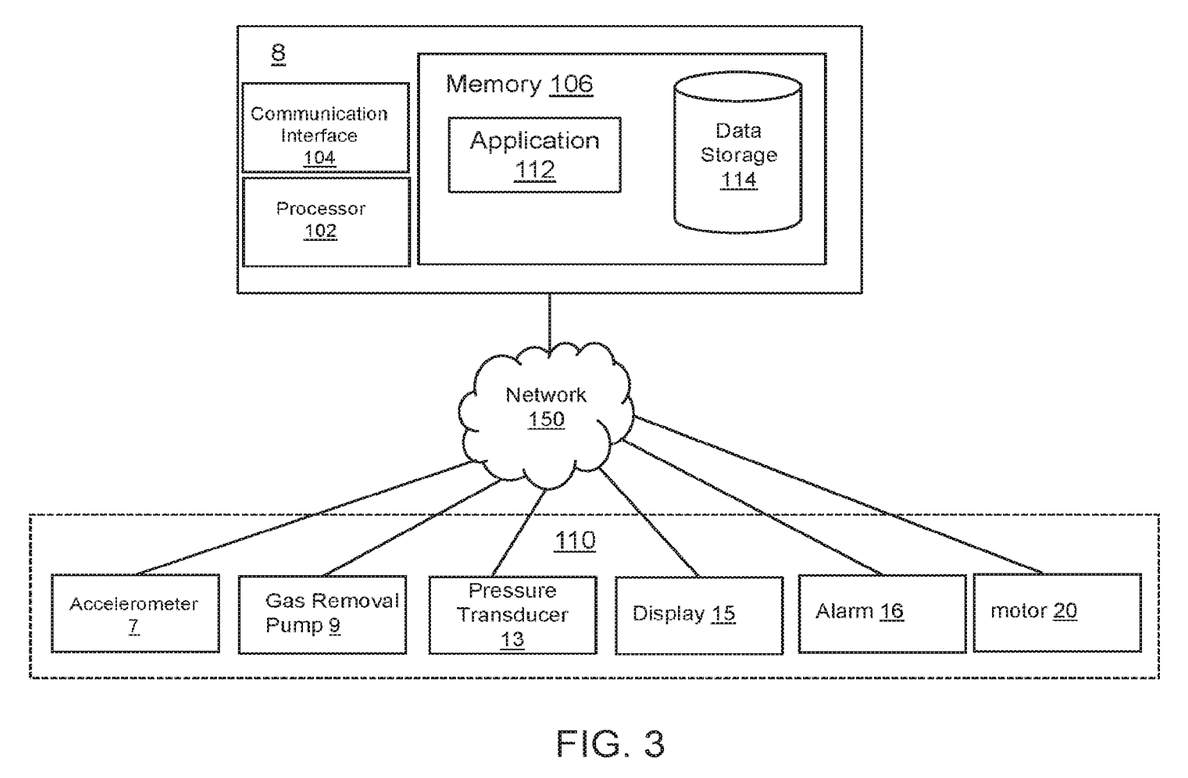
FIG. 3 illustrates a schematic view of a control system for gas removal from a wearable device, in accordance with an embodiment of the present application.

FIG. 3 shows an example system for gas removal from a wearable device. Gas removal system 100 may comprise a micro-controller. Controller 8 includes a processor 102 configured to implement processor readable instructions that, when executed, configure the processor 102 to conduct operations described herein. The processor 102 may be a microprocessor or microcontroller, a digital signal processing (DSP) processor, an integrated circuit, a field programmable gate array (FPGA), a reconfigurable processor, a programmable read-only memory (PROM), or combinations thereof. In a non-limiting example micro-controller may be provided by Microchip Technology Part #PIC16F18326T-I/JQ and supplied by Digikey Part # PIC16F18326T-I/JQCT-ND. The controller 8 includes a communication interface 104 to communicate with other computing or sensor devices, to access or connect to network resources, or to perform other computing applications by connecting to a network (or multiple networks) capable of carrying data. In some examples, the communication interface 104 may include one or more busses, interconnects, wires, circuits, and/or any other connection and/or control circuit, or combination thereof. The communication interface 104 may provide an interface for communicating data between the controller device 100 and a display 15 or an alarm 16. In some embodiments, the one or more busses, interconnects, wires, circuits, or the like may be the network of conductive and non-conductive fibers of a smart textile. An alarm described herein, may be any indication provided to a user of the wearable device that corrective action should be taken. Non-limiting examples of alarms are visual alerts on a display or a light of the wearable device; vibrations from a vibration actuator of the wearable device; or auditory alerts from a speaker of the wearable device.

Controller 8 may be coupled to the at least one of a an accelerometer 7, gas removal pump 9, pressure transducer 13, display 16, and/or alarm 16 via a network 150. The network 150 may include any wired or wireless communication path, such as an electrical circuit. In some embodiments, the network 150 may include one or more busses, interconnects, wires, circuits, and/or any other connection and/or control circuit, or a combination thereof. In some embodiments, the network 150 may include a wired or a wireless wide area network (WAN), local area network (LAN), a combination thereof, or the like. In some embodiments, the network 150 may include a Bluetooth® network, a Bluetooth® low energy network, a short-range communication network, or the like.

Controller 8 may include memory 106. The memory 106 may include one or a combination of computer memory, such as static random-access memory (SRAM), random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like.

The memory 106 may store an application 112 including processor readable instructions for conducting operations described herein. In some examples, the application 112 may include operations for detecting gas in the gas removal filter 2; detecting an orientation of the gas removal filter 2; measuring a pressure in the gas removal filter 2. The application 113 may also include operations for removing gas from the gas removal filter 2 when: gas is detected in the gas removal filter 2, and the orientation of the gas removal filter 2 is at an angle enabling gas within the gas removal filter to flow to the vent port (and vent tubing 10), for example the angle relative to the ground. Detecting gas in the gas removal filter 2 may be achieved with an ultrasonic gas detector configured to detect gas in the vent tubing 10; detecting the orientation of the gas removal filter 2 may be achieved with accelerometer 7; and removing gas from the gas removal filter 2 may be achieved with the gas removal pump 9. Removing gas from gas removal filter 2 may be initiated by application 112 automatically upon detecting orientation of gas removal filter 2 in an upright position and detecting gas in gas removal filter 2. In another example, application 112 may measure an interval between instances of removing gas from gas removal filter 2, and automatically initiate removing gas from gas removal filter 2 when a set time interval (e.g. 10 minutes) is exceeded, the gas removal filter 2 is in an upright position and gas is detected in gas removal filter 2.

In another example, application 112 may include an operation for terminating the removal of gas from gas removal filter 2 when a pressure drop is measured at pressure transducer 13. Continuing the example, as gas is withdrawn from gas removal filter 2, process fluid will follow the gas and be drawn through vent tube 10 to transducer protector filter 12. Application 112 may include an operation to determine if transducer protector 12 has been wetted, i.e. determining whether process fluid has been drawn to and is in contact with transducer protector filer 12, by monitoring the pressure at the pressure transducer 13 while gas removal pump 9 is withdrawing gas from vent tube 10. When transducer protector filter 12 becomes wetted, gas transfer through filter 12 may cease and pressure measured at the pressure transducer 13 will decrease rapidly or display a negative reading.

In another example, application 112 may include an operation for displaying the pressure measured by pressure transducer on display 15. Continuing the example, when gas removal filter 2 is filtering a process fluid, e.g. blood, and gas removal pump 9 is not withdrawing gas, the pressure measured by pressure transducer 13 may be venous pressure. Application 112 may include an operation to suspend display of the pressure measured by pressure transducer 13 when gas removal pump 9 is withdrawing gas from gas removal filter 2 and/or vent tubing 10. Alternatively, application 112 may temporarily freeze the display at the last recorded pressure measured by pressure transducer 13 before gas removal pump 9 begins withdrawing gas from gas removal filter 2 and/or vent tubing 10. Freezing the display during operation of gas removal pump 9 prevents display of pressure data affected by gas removal pump 9.

In another example, application 112 may include an operation for validating function of system 100. To validate function of system 100, application 112 may operate removal pump 9 in intervals for short periods of time to maintain a minimal interval of valid pressure readings from pressure transducer 13. Example pressure measurements may include measuring pressure at pressure transducer 13 when removal pump 9 is not running to determine the venous return pressure. An increase in the value of subsequent pressure measurements at pressure transducer 13 may indicate clotting of the gas removal filter 2, or excess unremoved air in gas removal filter 2 and/or vent tubing 10. If clotting of air removal filter 2 or excess unremoved air is detected, application 112 may include an operation to signal an alarm 16. Pressure measured at pressure transducer may also be affected by process fluid (i.e. blood) flow rate through inlet 1 and outlet 5, hematocrit of the blood (i.e. the ratio of solids to fluids in the blood which varies from patient to patient); return blood access patency (e.g. if a needle in a user is blocked by a blood vessel wall or a clot, the pressure at transducer 13 will rise). In dialysis, the effects of hematocrit and blood flow rate may be mitigated by application 112 that allows the blood pump to first run for about 10 seconds to establish a stable pressure with only hard limit alarms that stop the pump if the pressure exceeds a set value, e.g. 350 mm Hg. In other words, blood may be circulated from inlet 1 to outlet 5 while pressure within gas removal filter 2 stabilizes. After the initial stabilization period, application 112 may have narrower alarm limits, e.g. alarm limits set about 20 mm Hg above and below the stable pressure level. These narrower alarm limits are reset each time the pump (not shown) circulating proceed fluid, e.g. blood, is started or the blood pump rate is changed. In system 100, a rise in pressure at pressure transducer 13 may indicate either a problem with the needle in a user, or clotting in gas removal filter 2, vent tubing 10, and/or transducer protection filter 13. Gas removal filter may function as a retention filter to prevent passage of particulates released from fragmentation of components of the fluid circuit upstream of the filter. Gas removal filter may also function as a clot retention filter. The threshold for clotting detection may be the same, e.g. a pressure drop of approximately 20 mm Hg, depending on the blood flow rate being used. In an embodiment, system 100 comprises a second pressure transducer (not shown) on outlet 5 for determining a pressure downstream of gas removal filter 2 which can be used to distinguish clotting at gas removal filter 2 or a problem downstream of gas removal filter 2, e.g. a problem with a dialysis needle.

In another example, application 112 may include an operation for measuring the duration and flowrate of gas removed by the gas removal pump, and calculating the volume or mass of gas removed.

In another example, application 112 may include an operation for prompting a user of a wearable device, e.g. by sending a signal to alarm 16 and/or display 15, to orient the gas removal filter 2 into a upright orientation if a time interval since a valid upright orientation has occurred exceeds a set value. The set value may be pre-programmed into application 112 or may be input by a user with communication interface 104. In an example, a maximum time interval of 30 minutes may be the set value after which a signal would be sent to alarm 15 to alert a user to orient the system 100 in an upright position.

In another example, application 112 may cause gas removal pump 9 to run a reversal cycle to clear inlet 1 and outlet 5 between pressure tests. A reversal cycle may be initiated when system 100, and more particularly gas removal system 2, is in an upright orientation. In a normal (ideal) operation, gas (air) may continuously be sensed/detected by gas detector sensor 6, but a leak in system 100 could allow the level of the blood in gas removal filter 2 to rise until gas detector 6 no longer senses gas. If gas is not sensed at the gas detector 6, the gas removal pump 9 may run a predetermined length of time (in the reverse direction) to inject the process fluid, e.g. blood, back into gas removal filter 2 until gas is sensed at gas detector 6 again. If gas is not sensed/detected at gas detector 6 by the end of the reversal cycle, a check level alarm may be generated to alert the user, as the gas removal pump 9 may be not functioning properly, tubing may have become kinked or disconnected, or there may be a leak in the tubing or connections of system 100. The reversal cycle is different from a level test (discussed below) in that it does not initially run pump 9 to withdraw air from system 100 to raise the level of process fluid in gas removal filter 2 until gas is no longer sensed by the gas detector 6.

In another example, application 112 may initiate a level test. Gas removal pump 9 may be calibrated so that the volume of the gas that is pumped may be determined by how long the pump is switched on. Gas removal pump 9 may also withdraw gas from system 100 and pump gas into system 100 so that it may run to raise or lower the level of process fluid in gas removal filter 2. Gas detector 6 detects either the presence of gas in the vent tube 10 or detects no presence of gas. A level test may be initiated when system 100 is in an upright orientation. In a level test, application 112 may cause gas removal pump 9 to withdraw gas from the gas removal filter 2 causing the level of process fluid in the gas removal filter 2 to rise until it enters vent tube 10 near gas detector 6. When gas is not detected by gas detector 6, the gas removal pump 9 is stopped. Application 112 can then determine how much gas was in gas removal filter 2 by how long the gas removal pump 2 was operating. In this manner, application 112 can determine the level of process fluid in gas removal filter 2 based on the volume of the gas removal and initial pressure of said gas. In the next phase, gas removal pump 9 is reversed so that process fluid is pushed back into the gas removal filter 2 until gas is sensed at gas detector 6.

In another example, application 112 may monitor fluid circuit continuity. Fluid circuit continuity is the absence of any leaks, cracks or kinks in tubing or tubing connections. Typically, during dialysis, tubing that is before the blood pump is always under negative pressure and so any leaks in that location will allow air to enter the tubing. Further, any kinks in the tubing in the lines before the blood pump can cause a very significant negative pressure after the kink that may result in the deaeration of dissolved air present in the blood and so form bubbles in the blood. Monitoring fluid circuit continuity may be effected by monitoring the cumulative volume of air removed from system 100 over a period of time, and generating an alarm to request the patient to check the fluid circuit continuity if the cumulative volume of air removed from system 100 over the period of time is above a set value. The set value may be pre-programmed into application 112 or may be input by a user with communication interface 104. The volume of air removed may be calculated by the application 112 by multiplying the run time of the gas removal pump 9 by the flow rate of the gas removal pump 9. In an example, the flow rate of the gas removal pump 9 may be a constant value set for the pump, or may be measured by a flow element (not shown).

In another example, application 112 may include an operation for automatically correcting the orientation of gas removal chamber 2 or drip chamber 19 without user input. Application 112 may receive signals from at least one of accelerometers 7a, 7b indicating a tilt and/or roll of gas removal chamber 2 or drip chamber 19. Application 112 may then direct motors 20a, 20b to rotate gas removal chamber 2 or drip chamber 19 to an upright orientation. In an example, accelerometer 7a may measure a tilt of gas removal chamber 2 and application 112 may direct motor 20a to rotate about vector R1, i.e. the x-axis illustrated in FIGS. 4 and 5, such that gas removal chamber 2 (or drip chamber 19) is in an upright orientation. In another example, accelerometer 7b may measure a roll of gas removal chamber 3 and application 112 may direct motor 20b to rotate about vector R2, i.e. the z-axis illustrated in FIGS. 4 and 5, such that gas removal chamber 2 (or drip chamber 19) is in an upright orientation. In an embodiment, application 112 implements a closed-loop control system, e.g. a PID control system, where measurement signals received from accelerometers 7a, 7b are received by controller 8 causing application 112 to calculate an output value to send via a control signal to motors 20a, 20b for moving gas removal chamber 2 to a upright orientation. The control signals to motor 20a, 20b may be sent intermittently, e.g. after a desired time interval. A desired time interval may be the estimated time it would take to accumulate a give volume (or mass) of gas. In an example, measurement signals(s) may be received from accelerometers 7a, 7b, and control signal(s) may be sent to motors 20a, 20b every 20 minutes to move gas removal 2 to an upright orientation such that gas removal pump 9 may withdraw gas from the gas removal chamber 2. In another embodiment, measurement signal(s) may be sent to motors 20a, 20b to continuously maintain gas removal chamber 2 in an upright orientation which may be used in connection with the embodiment illustrated in FIG. 5 where liquid drip chamber 19 may need to be maintained in an upright orientation. In an example, measurement signal(s) may be received from accelerometers 7a, 7b, and application 112 may calculate an output value and send control signal(s) to motors 20a, 20b every 1 milliseconds to one second. In an example, measurement signal(s) may be received from accelerometers 7a, 7b, and application 112 may calculate an output value and send control signal(s) to motors 20a, 20b every 20 milliseconds.

Controller 8 may include a data storage 114. In some embodiments, the data storage 114 may be a secure data store. In some embodiments, the data storage 114 may store received data sets, such as orientation data, pressure data, flow rate data, or other types of data. In some examples, the data storage 114 may store data associated with criteria for analyzing received data sets. In some embodiments, the stored criteria may include pressure criteria that may be used for generating alarms that indications that pressure data may be trending beyond a defined pressure range.

Although the embodiments have been described in detail, it should be understood that various changes, substitutions and alterations can be made herein without departing from the scope. Moreover, the scope of the present application is not intended to be limited to the particular embodiments of the process, machine, manufacture, composition of matter, means, methods and steps described in the specification. The present disclosure may be embodied in other specific forms without departing from the subject matter of the claims. The present disclosure is intended to cover and embrace all suitable changes in technology. Modifications which fall within the scope of the present invention will be apparent to those skilled in the art, in light of a review of this disclosure, and such modifications are intended to fall within the appended claims. Also, the scope of the claims should not be limited by the preferred embodiments set forth in the examples, but should be given the broadest interpretation consistent with the description as a whole.

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

The description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

As can be understood, the examples described above and illustrated are intended to be exemplary only.

What is claimed is:

1. A system for gas removal from a wearable device, the system comprising:
   a gas removal filter having an inlet, a fluid outlet, and a vent port, the gas removal filter comprising:
   a filter mesh between the inlet and fluid outlet, the filter mesh configured to allow liquid phase material through the filter mesh and restrict gas phase material passing through the filter mesh;
   a gas detector for detecting gas in the gas removal filter;
   an orientation sensor for determining an orientation of the gas removal filter;
   a transducer protector filter having a first side and a second side, the transducer protector filter in fluid communication with the vent port of the gas removal filter;
   a pressure transducer in fluid communication with the second side of the transducer protector filter; and
   a gas removal pump in fluid communication with the second side of the transducer protector filter.

2. The system of claim 1 comprising a controller configured to perform a method comprising:
   detecting gas in the gas removal filter based on a signal from the gas detector;
   detecting orientation of the gas removal filter based on a signal from the orientation sensor;
   measuring a pressure in the gas removal filter based on a signal from the pressure transducer.

3. The system of claim 2 comprising removing gas from the gas removal filter when:
   gas is detected in the gas removal filter, and
   an orientation of a vent tube is at an angle enabling gas within the gas removal filter to flow to the vent port.

4. The system of claim 3, wherein the angle is generally perpendicular to the ground.

5. The system of claim 3, comprising terminating the removal of gas from the gas removal filter when a pressure drop is measured at the pressure transducer.

6. The system of claim 2, comprising detecting gas in the gas removal filter with an ultrasonic gas detector configured to detect gas in a vent tubing.

7. The system of claim 2, wherein said detecting orientation of the gas removal filter comprises detecting an orientation of the gas removal filter relative to the ground.

8. The system of claim 2, wherein the orientation sensor comprises an accelerometer.

9. The system of claim 2, comprising sending a signal to an alarm Ma when a pressure increase is measured above venous pressure.

10. The system of claim 2, comprising removing gas from the gas removal filter with the gas removal pump.

11. The system of claim 2, comprising measuring a duration and flowrate of gas removed by the gas removal pump, and calculating a volume or mass of gas removed.

12. The system of claim 2, comprising a mount coupled to a gas removal chamber, the mount providing at least two vectors of rotation which permit the gas removal filter to tilt and roll respectively, the mount comprising at least one motor for rotating the gas removal filter about the at least two vectors of rotation.

13. The system of claim 12 wherein the method comprises: measuring at least one of a tilt and a roll of the gas removal filter; calculating an output for the at least one motor to move the gas removal chamber to an upright orientation; and driving the at least one motor to rotate the gas removal filter to the upright orientation.

* * * * *